(12) United States Patent
Mbachu (10) Patent No.: US 7,641,826 B2
(45) Date of Patent: Jan. 5, 2010

(54) METHODS FOR MONITORING BINDER MIX LOADING OF FIBER GLASS MATS

(76) Inventor: Reginald A. Mbachu, 3950 Goodpasture Loop, Suite W112, Eugene, OR (US) 97477

( * ) Notice: Subject to any disclaimer, the term of this patent is extended or adjusted under 35 U.S.C. 154(b) by 655 days.

(21) Appl. No.: 11/356,175

(22) Filed: Feb. 17, 2006

(65) Prior Publication Data
US 2006/0138709 A1 Jun. 29, 2006

Related U.S. Application Data

(63) Continuation-in-part of application No. 11/008,097, filed on Dec. 10, 2004, now Pat. No. 7,128,867, which is a continuation of application No. 10/338,069, filed on Jan. 7, 2003, now Pat. No. 6,846,447, which is a continuation-in-part of application No. 10/294,296, filed on Nov. 14, 2002, now Pat. No. 6,846,446.

(51) Int. Cl.
*B29C 45/76* (2006.01)

(52) U.S. Cl. .................... 264/40.1; 264/406; 264/410; 264/488; 264/492

(58) Field of Classification Search ............. None
See application file for complete search history.

(56) References Cited

U.S. PATENT DOCUMENTS 3,196,072 A * 7/1965 Wirtz .................. 162/198
5,619,038 A * 4/1997 Parigi et al. ............ 250/339.12

* cited by examiner

*Primary Examiner*—Monica A Huson (57) ABSTRACT

Process and apparatus for non-invasive measuring of binder mix loading of glass fibers for monitoring production of construction insulation product, such as roofing and wall insulation. The process utilizes visible (VIS) and near infrared (NIR) spectroscopy; and, is particularly advantageous when utilized in an on-line production processing following binder mix loading of glass fibers and prior to curing treatment of the binder mix loaded glass fibers. Such spectroscopic analyses can be carried out on a static or moving support substrate. The blend is then conveyed to and through curing treatment to form insulation product. The blend is exposed to VIS-NIR radiant energy, and a radiant energy sensor collects resulting data as to absorption following penetration of the VIS-NIR radiant energy. The spectroscopic instrumentation is calibrated to determine to facilitate accuracy; and, can be used to verify load following curing. The amount of binder mix, in the binder mix/fiber blend, is adjusted if the blend is outside of desired loading specifications.

19 Claims, 3 Drawing Sheets

METHODS FOR MONITORING BINDER MIX LOADING OF FIBER GLASS MATS

RELATED APPLICATIONS

The present application is a continuation-in-part of U.S. Ser. No. 11/008,097 filed Dec. 10, 2004 entitled "METHODS OF MONITORING RESIN-LOADING OF WOOD MATERIALS AND ENGINEERED PRODUCTS" which is now U.S. Pat. No. 7,128,867 B2, which is in turn a continuation of Ser. No. 10/338,069 filed Jan. 7, 2003, entitled "METHODS OF MONITORING RESIN-LOADING OF WOOD MATERIALS AND ENGINEERED PRODUCTS", now U.S. Pat. No. 6,846,447 B2, which in turn is a continuation-in-part of Ser. No. 10/294,296 filed Nov. 14, 2002 entitled "NIR SPECTROSCOPIC MONITORING OF RESIN-LOADING DURING ASSEMBLY OF ENGINEERED WOOD PRODUCT", now U.S. Pat. No. 6,846,446 B2, which are incorporated herein by reference.

INTRODUCTION

The present invention relates to methods for monitoring binder mix loading of fiber glass during assembly of mats for production of insulation products useful in construction, e.g., roofing insulation, wall insulation and the like. In particular, the invention is concerned with use of visible (VIS) near infrared (NIR) radiant-energy spectroscopy for quantitatively measuring and maintaining binder mix loading within designated manufacturing standards.

OBJECTS OF THE INVENTION

An important object provides for calibrating visible (VIS) near infrared (NIR) spectroscopic instrumentation for accurate and prompt measurement of binder mix loading during assembly of binder mix loaded fiber glass mats.

A related object provides for monitoring binder mix loading of fiber glass during assembly of mats for insulation product.

Another object is to provide on-line measurement of binder mix loaded fiber glass mats as assembled prior to subsequent processing, e.g., curing.

A related object provides for feedback of binder mix loading data to maximize continuing on-line assembly, within manufacturing standards, and to optimize binder mix usage.

The above objects and other contributions of the invention are considered in more detail in describing the invention in relation to the accompanying drawings.

DETAILED DESCRIPTION OF THE INVENTION

In order to manufacture quality fiber glass mats using binder mixes, consistent application rates, on glass fibers for making fiber glass mats, are important. The ability to accurately monitor and promptly control application rates ensure product homogeneity, minimizes out-of-specification products, and optimizes binder mix usage. In manufacturing binder mix loaded fiber glass mats, the binder mix is generally applied by atomization. In prior practice, use of binder mix is measured by an in-line flow meter; and, binder mix losses due to lost vapor, build-up equipment, and the like are not taken into account.

The present invention provides for measuring binder mix as loaded on glass fibers, following binder mix application; and, prior to subsequent processing so as to provide a finished product for construction insulation; such as, roofing insulation, wall insulation, and the like. That sequence provides for early detection of out-of-specification material, which in turn provides for adjustment of binder mix application, so that the application rate can be corrected so as to promptly bring the binder mix loaded glass fibers within specifications. That results in savings as to material, time and, thus, cost.

The invention is directed to non-invasive on-line monitoring of binder mix loading, during assembly of fiber glass mats utilizing spectroscopic quantitative analysis. The term "binder mix loading" is used interchangeably with "binder mix content"; and, binder mix loading can be indicated as a weight percentage in relation to the weight of the fiber glass material.

Quantitative spectroscopy analyses utilizing calibrated instrumentation measures the interaction of radiant-energy, in a selected wavelength range of 350-2500 nanometer (nm), which penetrates the fiber glass materials. While the entire wavelength of 350-2500 nm can be measured and processed to determine binder mix loading of fiber glass material, the processing time and instrumentation necessary to carry out the measuring and processing can be decreased by measuring and processing only select wavelengths within the range of 350-2500 nm. Individual wavelength regions providing accurate results are (i) 400-1000 nm, (ii) 400-1800 nm, and (iii) 400-2500 nm. Measuring time is decreased since a lesser number of wavelengths are utilized and processing time is decreased since less data need be collected and processed.

Calibration of VIS-NIR spectroscopic instrumentation, in accordance with the invention, involves measuring radiant-energy absorption by measuring reflected non-absorbed radiant-energy, across the full VIS/NIR range, or, selected spectral range portions; and, correlates such measurement with binder mix loading. A unique advantage provided by the present invention is that on-line monitoring of binder mix loading is non-invasive of the fiber glass material and, therefore, on-line application of binder mix on fiber glass material and processing and production can proceed without interference because of binder mix loading measurements; that is, except when such measurements, determined in accordance with the invention, indicate that binder mix loading is not within designated manufacturing standards.

A spectrometer serving as a sensor, or detector, measuring VIS-NIR wavelength absorption to determine binder mix loading of a fiber glass material can vary depending on the spectral wavelength range being utilized. A preferred sensor for the 350-1050 nm range comprises a silicon photodiode detector; for a 1000-1800 nm range comprises an Indium/Gallium/Arsenide (InGaAs) single spectrometer; for a 1000-2500 nm range comprises an InGaAs dual spectrometer; and, for the complete 350-2500 nm range comprises a silicon and InGaAs photodiode array. Alternatively, when a range of 400-2500 nm is to be measured a lead sulfide spectrometer can be utilized.

The invention measures binder mix loading of fiber glass. Fiber glass mats are made of glass fibers held together by such binders. Binders are conventionally composed of either phenolic, amino, or acrylic-based binder mixes, with other conventional adjuvant ingredients which provide a binder mix. In order to manufacture quality products using a binder mix, consistent application rates on glass fibers are important. Controlling application rates ensures product homogeneity, minimizes out-of-specification product, and optimizes binder use. Binder mix application and monitoring can vary by product. In manufacturing insulation siding, for example, the binder mix is often atomized with an air sprayer as the glass fiber falls or is blown past the sprayer nozzle. Application is measured by previously-mentioned in-line flow meters. Any losses of binder mix due to lost vapor, container wall buildup, etc. are not taken into account. Further, in prior practice, binder mix application rate was determined by weighing a selected portion of the binder-mix-loaded fiber glass; then burning that portion in a furnace at around 650° C.; and then, measuring the loss in weight of the remaining fiber glass. Such percent loss in weight (often called "percent loss on ignition", or % LOI), was used to indicate binder mix applied to the fiber glass mat. That process is labor intensive, can give as much as 20% variation between tests, and, with testing as little as once every two hours, is unreliable, that is, at least four hours of production material is suspect with one low reading.

The purpose of insulation is to slow down the movement of heat through the walls of a building. Fiber glass insulation is made from very fine strands of fiber glass held together randomly in a thick mat. Fiber glass strands are very poor conductors of heat; such that any heat transfer through the fiber glass mat must be accomplished by convection randomly through tiny air pockets in the fiber glass mat. The insulating properties of fiber glass mat depend on that random path. If the mat is compressed, the path becomes shorter, and the insulation diminishes.

The invention enables real-time monitoring of binder mix concentration on fiber glass mat using selected spectral ranges of a combination of VIS-NIR spectroscopy, and selected multivariate calibration algorithm. The unique features of this invention include: measurement of binder mix absorption in the entire VIS-NIR region (350-2500 nm), calibration using binder mix absorption wavelengths and multivariate calibration algorithm rather than simple linear regression.

In the invention, the percent of binder mix on a fiber glass mat can be determined by correlating the amount of binder mix applied on the fiber glass substrate to binder mix absorption utilizing the entire VIS-NIR spectral range. Rather than a simple linear regression of data, a multivariate calibration algorithm (e.g. Partial Least Squares or PLS) is used to correlate binder mix loading to VIS-NIR absorption. That calibration algorithm removes matrix effect of the substrate leaving the net change in VIS-NIR absorption responsive to binder mix. That type of calibration yields a high degree of precision and gives a precise measurement of binder mix content.

Previously, % Loss On Ignition (or % LOI) was determined by the amount of binder mix lost by heating a known weight of binder mix loaded fiber glass at 650° C. for 2.0 minutes. Visible (VIS)-Near-Infrared (NIR) Quantitative spectroscopic analysis involves the interaction of VIS and NIR radiant energy with matter, wherein measurement is made in the full 350-2500 nm wavelength region of the electromagnetic spectrum Multivariate calibration procedures involve many variables; and Partial Least Squares (PLS) is a complex mathematical procedure in which many absorption wavelengths and concentrations are regressed simultaneously.

Suitable binder mixes for use with glass fiber mats include amino-formaldehyde-based binder mixes such as urea-formaldehyde binder mix, phenolic binder mixes, and acrylic-based binder mixes such as polyvinyl acetate and polyvinyl alcohol. The binder mixes are preferably in a liquid form to facilitate atomizing for fluidized applications; some powdered binder mixes can be used provided atomized fluidization is not disturbed. Other additives can also be added while avoiding atomizing difficulties for binder mix loading of the invention.

Figure 1:
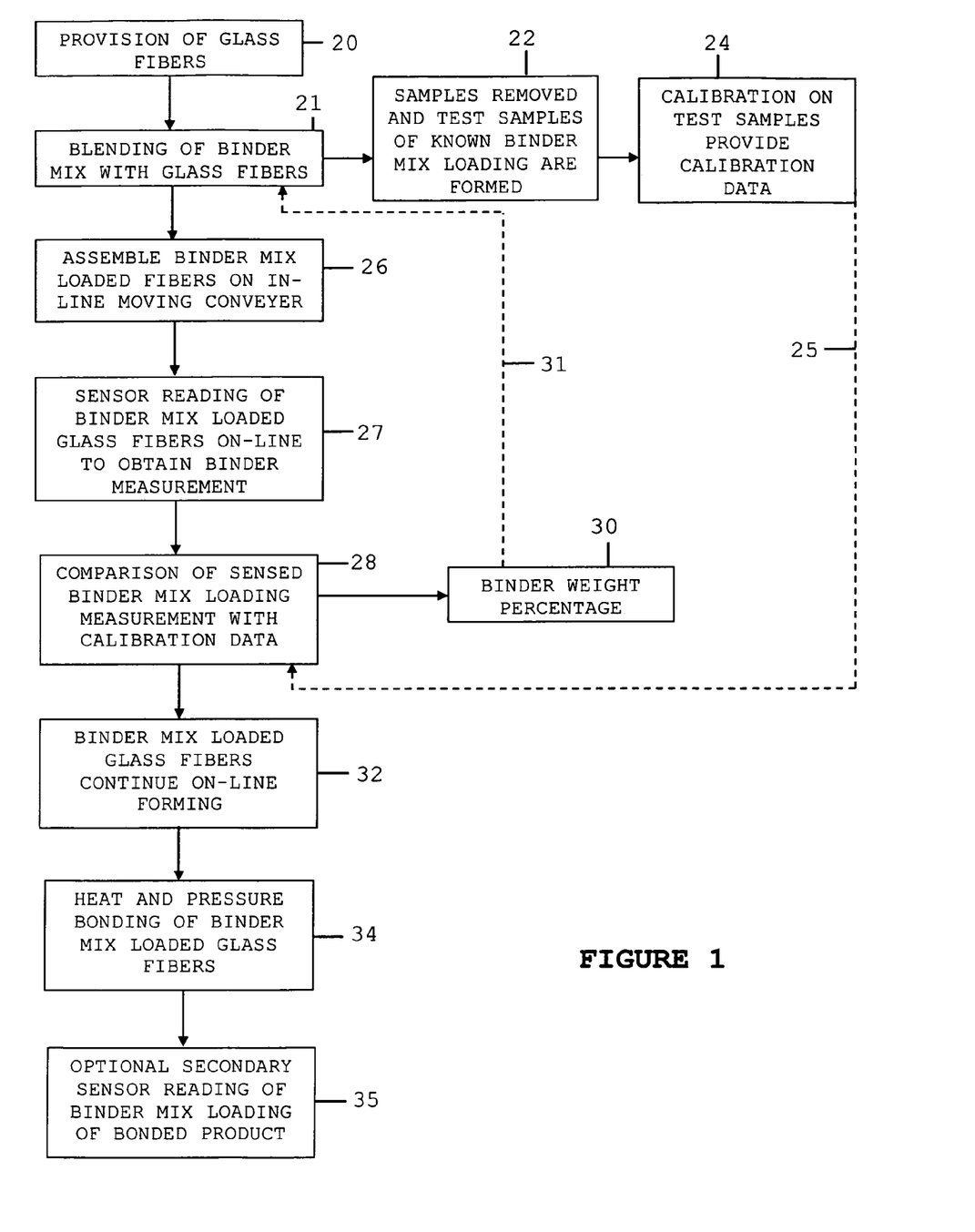
FIG. 1 is a block diagram for describing on-line processing in accordance with the invention for production of binder mix loaded fiber glass mats.
Figure 2:
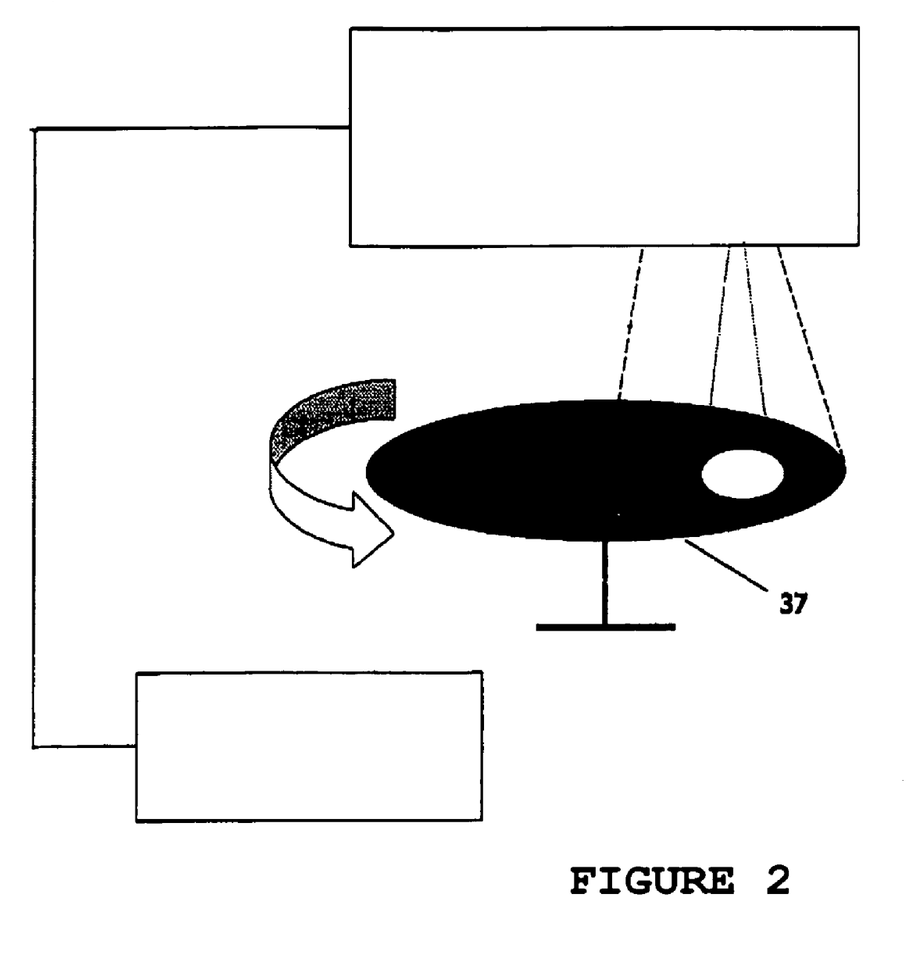
FIGS. 2 and 3 are schematic presentations of apparatus for carrying out the invention during batch production operations.
Figure 3:
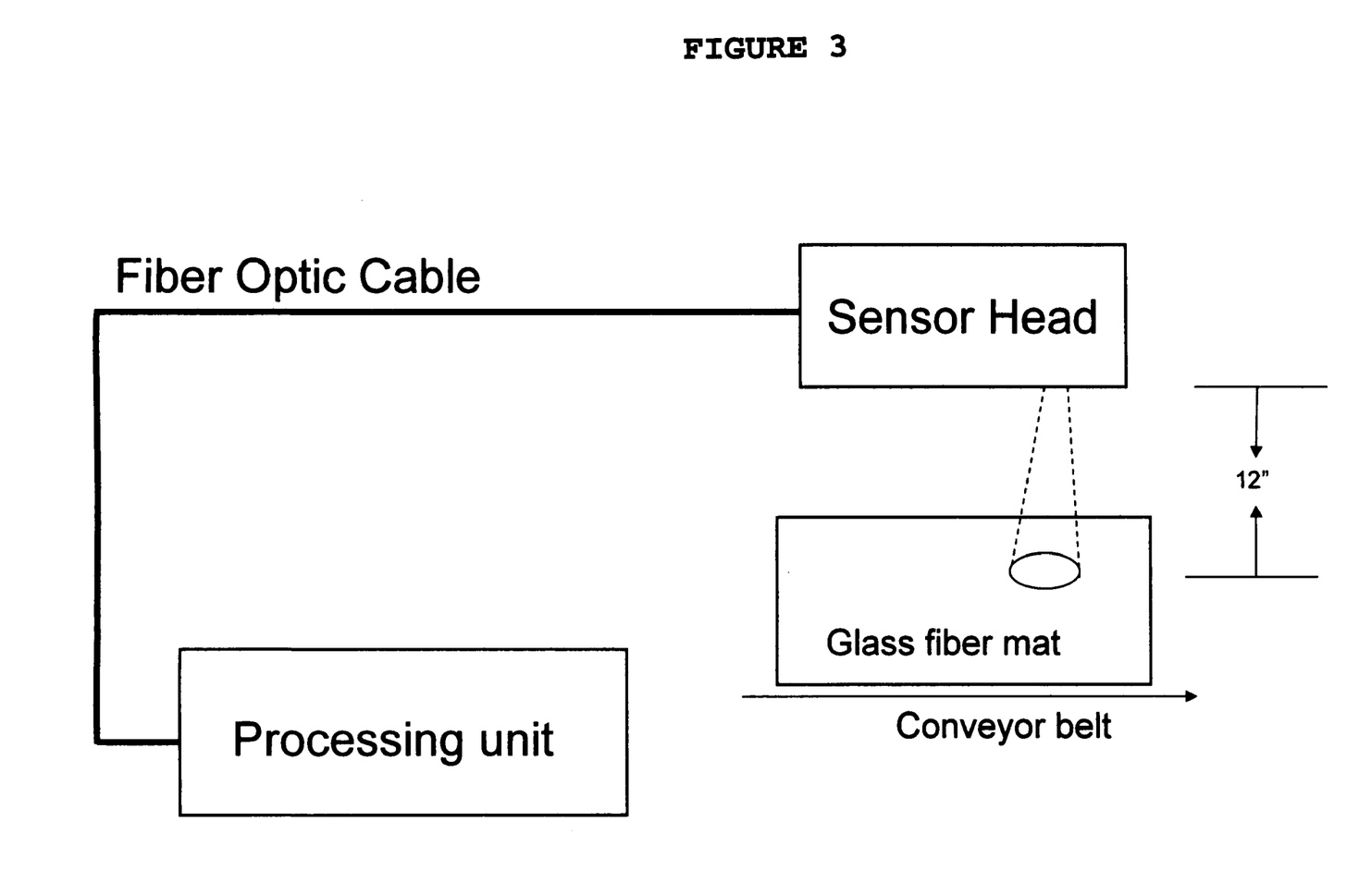

Assembly and measurement steps of the invention are described in relation to FIGS. 1, 2 and 3. In FIG. 1, glass fibers are provided at station 20; and, directed for blending with binder mix at station 21.

Calibration, for in-line VIS-NIR spectroscopic instrumentation, is initiated at station 22. Sample materials are selected for establishing known binder mix-content reference-source test-samples. Samples are selected, by making static chemical test measurements for binder mix loading weight, in relation to weight of glass fibers. Preferably, incrementally progressive binder mix loading samples of zero percent to forty percent (40%) are selected. Calibration of the VIS/NIR spectroscopic instrumentation is then carried out at station 24 as described later herein. The calibration data is directed over interrupted-line 25 for use in the assembly line, as described below.

At station 26 in the assembly line, binder mix loaded fibers are placed on an in-line conveyance system. The blend of fibers and binder mix are formed into a mat to form a continuous mat of glass fibers, which is moving toward ultimate bonding by curing. Non-invasive monitoring of the binder mix loaded fibers is carried out by VIS-NIR spectroscopic instrumentation at station 27. Non-absorbed reflected VIS-NIR energy is measured by the instrumentation sensor. The sensor is positioned above the moving line, preferably about 5-12 inches above the binder mix loaded blend on the assembly line. The VIS-NIR source of radiant energy covers a selected area of about three to about twenty four square inches; the VIS-NIR energy of the selected wavelength range penetrates the binder mix loaded blend by at least about two to five mm.

The return reflected VIS-NIR energy is collected fiber-optically and processed by calibration data at station 28; calibration data is received over interrupted-line 25, from station 24. The calibration measurement of binder mix loaded percentage weight is indicated at station 30. Correction, if any, of binder mix loading can be directed manually, or automatically over interrupted-line 31, to binder mix loading station 21. The binder mix loading weight percentage can be adjusted; also, the assembly line-speed can be adjusted.

The binder mix loaded glass fiber mat at station 32 continues toward curing at station 34. If desired a secondary sensor can be positioned at station 35, after curing treatment, to measure binder mix loading of the bonded product; providing an added confirmation that the bonded product is within specifications.

In the non-invasive on-line non-contact monitoring of binder mix loading of glass fibers using VIS-NIR spectroscopy, calibration is based on multivariate calibration; such as, for example, using multiple wavelength correlation techniques such as: Partial Least Squares (PLS), Principle Component Regression (PCR), or Multiple Linear Regression (MLR). PLS is preferred; it has been determined that PLS provides a better correlation coefficient and higher accuracy. Use of PLS in the calibration of the invention, simultaneously regresses VIS-NIR absorption wavelengths and concentrations of the binder mix facilitating correlation with the binder mix loading.

The calibration method of the invention can be conducted either in a laboratory on a batch basis to determine treatment parameters for use on-line; or, in an on-line continuous manufacturing operation. FIG. 2 shows use of a batch basis using a rotatable turntable 37; or, alternatively, an arrangement of a blend of binder mix and glass fiber placed positioned for simulating moving line material to be monitored.

FIG. 3 shows a schematic of a VIS-NIR setup of a glass fiber mat in relation to a conveyer belt. Calibration and monitoring of the glass fiber mat material is carried out as described in relation to calibration and monitoring of the on-line material. Calibration is conducted for each line of blended material to be monitored, since variation can occur between different blends. Calibration utilizing reference samples, taken from the blend to be tested, facilitate achieving desired accuracy.

During calibration, direct measurements are made from test samples where the amount of binder mix has been pre-established. The resulting calibration data are correlated with measurements obtained from binder mix loaded glass fibers as batch processed or an on-line manufacturing process. If differences are present, it is known that out-of-specification material is being presented and corrective action is necessary.

The invention utilizes VIS-NIR spectroscopy chemometric quantitative measurements of binder-mix loading. Calibration data, for use in later processing, is developed utilizing a calibration model, such as Partial Least Squares (PLS). Parameters or factors are chosen based on the system parameters of the process being monitored. A sufficient number of factors are selected to provide for reliable comparison and correlation of data between the model and an unknown. Beyond a certain number of factors, the difference monitored is minimal as to become inconsequential; such added factors need not be considered. The number of factors to be used can be determined using a trial batch analysis. That calibration is utilized to determine concentrations of binder mix present in the glass fiber/binder mix blend during processing.

Software useful to collect data, upon monitoring a blend, is commercially available under the name "Indico Pro", version 6.0 as marketed by Analytical Spectral Devices (ASD). Software useful to process the data collected is also commercially available under the name GRAMS/A1, version 7.02 as marketed by Thermo Electron Corporation. A VIS-NIR instrument useful as a sensor for providing exposure to VIS-NIR energy and collecting the spectra from the material exposed is sold by Applied Spectral Devices under the name "QualitySpec Pro"; and, is capable of collecting spectra of the entire VIS-NIR region at a rate of 10 scans per second. Depending on wavelength, VIS-NIR radiant energy penetrates 2-5 mm into the glass fiber/binder mix blend. The blend is illuminated with VIS (NIR) spectrum light from a lamp mounted on the sensor head. Energy returning from the blend is received by the sensor and then transmitted to a processing unit, such as a monochromator, via a fiber optic bundle or single fibers attached to the sensor head, where it is broken down by wavelengths.

Operation of the invention is based on the assumption in chemometrics that light absorption is related to concentrations of the constituents of interest; in theory chemical bonds, such as C—H, C—C, N—H, etc., cause molecular vibrations. At low energy levels those molecular vibrations are harmonic and lead to the transition of one allowed energy level. Such fundamental transition is manifested by absorption in the mid-IR region. However, at higher vibrational levels, molecular vibrations become anharmonic and lead to two or more transitions resulting in absorption in the NIR region. Thus, near infrared absorptions comprise overtones and combination bands.

Depending on the wavelength, the NIR energy penetrates 2-5 mm into the sample. A Direct VIS Light system illuminates the sample with full-spectrum VIS light from a lamp mounted in the sensor head. The NIR energy is selectively absorbed by the sample based on its chemical makeup and levels of constituents. Energy returning from the sample is then returned to the monochromater, via a fiber optic bundle attached to the sensor head, where it is broken down into NIR energy. The wavelengths at which the constituents absorb energy are monitored through software for their relative peak intensity. The peak shape is converted to a level of analyte and the information is collected on the computer for use in process adjustment.

Method steps of the invention carried-out for binder mix loading on glass fibers for making fiber glass insulation are described below. The examples also set forth data for illustrating measurement accuracy of the invention.

EXAMPLE

Binder Mix Loading on Glass Fibers

Binder mix loaded fiber glass mat samples with different % LOIs were prepared and analyzed for the purpose of developing calibration curves for use in predicting unknown samples. Two types of insulation binders were used; the first was manufactured with phenol-formaldehyde (PF) binder mix A and the other was made with PF binder mix B. For the insulation binders, the percent Loss on Ignition (% LOI) values used for calibration ranged from 3.37 to 25.6%. The range of calibration samples for roofing mat urea-formaldehyde (UF) binders was 7.56 to 35.5%. A UF binder mix is referred to as "C". Percent LOI values for the primary method were determined by ashing known weights from different sections of a fiber glass mat and averaging the loss in weight of the mat samples after ashing at 650° Centigrade.

Six unknown binder mix loaded fiber glass mat samples were used to validate the calibration curves. Spectral data were collected with an ASD QualitySpec instrument equipped with a sensor head and connected to a fiber optic bundle. The sensor head was mounted at a distance of 12 inches above the horizontal fiber glass mat samples. Data was collected in the 400-2500 nm spectral range.

Results with NIR spectroscopy and Partial Least Squares (PLC) multivariate calibration algorithm accurately determine the binder concentration (% LOI) of fiber glass mats useful as wall and roofing insulation. The calibration curves constructed with the laboratory fiber glass mat standards were successfully used to predict the binder concentration of six unknown samples manufactured in the laboratory to an accuracy better than 1% LOI.

In order to obtain the most robust calibration, calibration curves were constructed with reflectance and first derivative spectra. In addition, different wavelength regions were used for calibration to find the most suitable calibration algorithm and wavelength region for use in prediction of unknown samples. Results indicate that both reflectance and first derivative calibration were adequate in predicting unknown samples. For the PF binder mix used for the insulation samples, the calibration curve based on reflectance in the visible NIR region between 400-1800 gave the best results. For the UF binder mix used for the roofing mats, the inclusion of the high wavelength regions containing the amino functional groups was necessary to obtain good calibration predictability of unknown samples. Thus, the 400-2500 nm region performed the best in the reflectance mode. In all cases, the models analyzed unknown laboratory samples to an accuracy of better than 1% LOI (absolute).

Procedure

Sample Preparation of PF Insulation and UF Roofing Fiber Glass Mats

Two different binder solutions (A and B) were used to prepare the insulation fiber glass mat wall insulation samples for NIR calibration. A third binder solution (C) was used for the roofing mat. The different binder mixes including a binder, as set forth, with additives conventionally referred to as carriers. More particularly, the binder mix solutions A, B and C include:

| Binder Mix A | Binder Mix B | Binder Mix C |
|---|---|---|
| Phenolic binder mix | Phenolic binder mix | Urea-formaldehyde binder mix |
| Additives | Additives | Latex carrier |

The phenolic binder can be phenol formaldehyde. A spray gun was used to apply the liquid binder solution. All binder mix loaded fiber glass mats (wall insulation and roofing mats) were cured at 200° C. for 2.5 minutes.

For instrument calibration, % LOI of standards was obtained by weighing the fiber glass after burning off the binder mix from the fiber glass at 650° C.

Fiber glass mats were placed on a dark stationary background 12"×12" square and a NIR sensor head was placed 12" directly above the fiber glass mat. The sensor head was suspended on a tripod and the NIR spectral data was obtained using Indic Pro software supplied with the instrument.

Calibration

Two types of Partial Least Square (PLS) calibration, reflectance and first derivative, curves were constructed with the NIR absorption spectra and the binder loading values at different wavelengths in the 400-2500 nm region. The reflectance calibration utilized the measured absorption without any mathematical treatment. The first derivative calibration takes the first derivative of the absorption spectra and uses these values for regression. All the other calibration curves look similar with differences in the degree of fit and factors as detailed in Tables 1-3. Tables 1-3 show the $R^2$ contribution and standard error of cross validation (SECV) at different factors. The standard error term is based on the units of calibration. This value generally becomes smaller as the regression factor increases for a particular calibration. The use of more factors to improve the correlation and the coefficient of regression does not necessarily provide for more accurate calibration. To select the optimum number of factors to use in a calibration model, it is useful to look at the spectral plots of the loadings, which are derived from second derivative spectra of the samples. Loadings describe the variation being modeled by each factor. The first factor has the highest loading intensity, and usually decreases for each subsequent factor. When the loadings no longer appear to model components of the sample, the factors they represent cease to improve the calibration. Tables 1-3 show the optimum suggested factors in each wavelength region.

TABLE 1

Calibration Parameters For Insulation Binder Mix With PF Binder Mix A

| Sample | Wavelength, nm | Reflectance | | | 1st Derivative | | |
|---|---|---|---|---|---|---|---|
| | | Factors | SECV | $R^2$ | Factors | SECV | $R^2$ |
| A | 400-2500 | 7 | 0.49 | 0.9967 | 4 | 0.651 | 0.9944 |
| | 400-1800 | 9 | 0.441 | 0.9973 | 7 | 0.442 | 0.9974 |
| | 400-1000 | 10 | 0.4 | 0.9976 | 8 | 0.397 | 0.9979 |

TABLE 2

Calibration Parameters For Insulation Binder Mix With PF Binder Mix B

| Sample | Wavelength, nm | Reflectance | | | 1st Derivative | | |
|---|---|---|---|---|---|---|---|
| | | Factors | SECV | $R^2$ | Factors | SECV | $R^2$ |
| B | 400-2500 | 5 | 0.63 | 0.9967 | 3 | 0.543 | 0.9944 |
| | 400-1800 | 10 | 0.377 | 0.9973 | 10 | 0.368 | 0.9974 |
| | 400-1000 | 9 | 0.301 | 0.9976 | 9 | 0.371 | 0.9979 |

TABLE 3

Calibration Parameters For Roofing Mat Binder Mix With UF Binder Mix C

| Sample | Wavelength, nm | Reflectance | | | 1st Derivative | | |
|---|---|---|---|---|---|---|---|
| | | Factors | SECV | $R^2$ | Factors | SECV | $R^2$ |
| C | 400-2500 | 4 | 1.00 | 0.9921 | 2 | 0.919 | 0.9944 |
| | 400-1800 | 9 | 0.922 | 0.9482 | 5 | 1.110 | 0.9974 |
| | 400-1000 | 8 | 1.690 | 0.9970 | 8 | 2.260 | 0.9979 |

The low values of the SECV and high $R^2$ in the 400-1800 and 400-1000 nm regions of Tables 1 and 2 suggest that these regions are more suited than the full wavelength region (400-2500 nm) for calibration of a phenolic binder mix.

As for the Roofing mat binder, the long wavelength NIR region appears to be more important for accurate calibration since that region (400-2500 nm) gives the lowest SECV. The calibration curves constructed with the reflectance and first derivative data at different wavelengths were used to predict unknown samples. For each binder mix two unknown samples were used for the prediction.

Prediction of Unknown Samples Manufactured by Batch

The NIR predicted values and the measured values for the unknown samples are detailed in Tables 4-6. The NIR computed values show excellent agreement with the measured values. For the wall insulation samples, the regions 400-1000 nm and 400-1800 nm give the closest match to the unknown samples irrespective of whether a reflectance or first derivative calibration is used (Tables 4-5). For these samples which use colored PF binder mixes, the visible region plays an important part in accurate calibration and prediction. Although the 400-1000 nm region gives the closest match to the unknown, the 400-1800 nm region, in general, has the lowest standard deviation of prediction, M-Distance (Mahalanobis distance), and F-Ratio. The significance of the short wavelength NIR regions is that low cost instruments based on these regions should be adequate for this application.

For the roofing mat binder, the 400-2500 nm region, in general, gives the lowest standard error of prediction and lowest M-Distance of the three regions used for prediction (Table 6).

TABLE 4

Prediction Results Of Unknown Samples Manufactured With Binder Mix A

| Sample ID A | Wavelength (nm) | Reflectance Spectra | | | 1st Derivative | | | Measured |
|---|---|---|---|---|---|---|---|---|
| | | % LOI | M-Distance | F-Ratio | % LOI | M-Distance | F-Ratio | % LOI |
| UNKNOWN-1 | 400-2500 | 17.21 ± 0.40 | 0.92 | 1.401 | 17.33 ± 0.55 | 0.95 | 1.362 | 18.24 ± 1.54 |
| | 400-1800 | 17.37 ± 0.30 | 0.86 | 1.139 | 17.23 ± 0.36 | 0.59 | 1.106 | |
| | 400-1000 | 17.53 ± 31 | 1.54 | 1.754 | 17.59 ± 0.28 | 1.26 | 1.74 | |
| UNKNOWN-2 | 400-2500 | 9.85 ± 0.49 | 1.82 | 1.974 | 10.17 ± 0.39 | 1.17 | 1.541 | 8.07 ± 0.89 |
| | 400-1800 | 9.35 ± 0.35 | 1.61 | 1.929 | 9.24 ± 0.40 | 1.18 | 1.803 | |
| | 400-1000 | 9.21 ± 0.18 | 1.86 | 2.094 | 9.36 ± 0.24 | 1.33 | 1.737 | |

TABLE 5

Prediction Results Of Unknown Samples Manufactured With Binder Mix B

| Sample ID Insul B | Wavelength (nm) | Reflectance Spectra | | | 1st Derivative | | | Measured |
|---|---|---|---|---|---|---|---|---|
| | | % LOI | M-Distance | F-Ratio | % LOI | M-Distance | F-Ratio | % LOI |
| UNKNOWN-3 | 400-2500 | 22.44 ± 0.30 | 1.07 | 0.956 | 22.05 ± 0.50 | 1.14 | 1.02 | 22.15 ± 1.08 |
| | 400-1800 | 21.90 ± 0.31 | 1.04 | 1.26 | 21.91 ± 0.50 | 0.96 | 1.25 | |
| | 400-1000 | 21.83 ± 0.57 | 1.56 | 1.684 | 21.95 ± 0.45 | 1.26 | 1.5 | |
| UNKNOWN-4 | 400-2500 | 8.69 ± 0.18 | 0.76 | 1.141 | 8.37 ± 0.22 | 0.89 | 1.039 | 7.52 ± 0.95 |
| | 400-1800 | 8.25 ± 0.20 | 1.13 | 1.566 | 8.29 ± 0.07 | 0.75 | 1.336 | |
| | 400-1000 | 8.07 ± 0.25 | 1.2 | 1.622 | 8.11 ± 0.14 | 0.94 | 1.457 | |

TABLE 6

Prediction Results Of Unknown Samples Manufactured With Binder Mix C

| Sample ID | | Reflectance Spectra | | | 1st Derivative | | | |
|---|---|---|---|---|---|---|---|---|
| Roofing mat C | Wavelength (nm) | NIR % LOI | M-Distance | F-Ratio | NIR % LOI | M-Distance | F-Ratio | % LOI Actual |
| UNKNOWN-5 | 400-2500 | 28.28 ± 0.53 | 0.72 | 0.936 | 27.91 ± 0.53 | 0.76 | 0.930 | 30.21 ± 2.82 |
| | 400-1800 | 27.64 ± 0.86 | 0.73 | 1.14 | 26.78 ± 0.52 | 0.51 | 0.748 | |
| | 400-1000 | 28.95 ± 1.74 | 0.98 | 1.504 | 25.68 ± 2.21 | 0.98 | 1.509 | |
| UNKNOWN-6 | 400-2500 | 16.78 ± 0.29 | 0.65 | 1.041 | 17.27 ± 0.52 | 0.41 | 1.041 | 17.71 ± 0.83 |
| | 400-1800 | 17.63 ± 0.23 | 0.86 | 1.327 | 16.78 ± 0.46 | 0.48 | 0.900 | |
| | 400-1000 | 19.11 ± 1.26 | 1.24 | 1.477 | 15.92 ± 1.43 | 0.99 | 1.488 | |

The results and date detailed above demonstrate that near infrared technology can be successfully used to monitor % LOI of unknown samples; in particular when the fiber glass matrix used to calibrate the instrument is similar to that used to manufacture the unknown samples. The standard error of prediction establishes that the instrumentation can predict unknown samples to an accuracy of better than 0.6%. When working with binder mix solutions containing a PF binder, the 400-1800 nm region provides the best results when working binder mix solutions containing amino binder, e.g. UF, the full wavelength region, 400-2500 nm, provides the best results.

The calibration method of the invention is independent of the glass fiber type. The glass fiber is a constant since the changes measured are only with respect to the amount and type of binder mix.

The above disclosure is detailed so as to enable one skilled in the art to practice the invention. It should also be recognized that more changes, in particular with regard to percentages of various constituents, or minor changes in timing, or by substituting equivalent techniques fall within the protected scope of the invention as set forth in the appended claims; and that such claim terminology shall be interpreted from the above disclosure.

The invention claimed is:

1. Process for monitoring binder mix loading of glass fibers comprising
   (a) providing a first blend combining glass fibers and binder mix, each in an amount suitable for forming insulation product;
   (b) exposing samples of said first blend, while on a static support substrate or on a moving support substrate, to radiant energy in a wavelength region of about 350-2500 nm, and spectroscopically collecting data resulting from penetration of such energy into said first blend of such samples; for
   (c) providing calibration of spectroscopic instrumentation, based on the data collected in (b), so as to enable reflecting binder mix content of such samples;
   (d) placing a second blend of glass fibers and binder mix on a predetermined support substrate;
   (e) subjecting, free of mechanical contact with said second blend, at least a portion of said second blend to radiant energy in a wavelength spectrum of about 350-2500 nm, for measuring absorption data reflecting absorbed energy into said second blend; in which
   (f) such measured absorption data of (e) is correlated with said calibration of (c) for verifying quantitative measurement of hinder mix content of said second blend.

2. The invention of claim 1, wherein steps (e) and (f) are conducted on a periodic or a continuous basis.

3. The invention of claim 1, wherein said second blend is provided as a mat.

4. The invention of claim 1, wherein said calibration of said spectroscopic instrumentation is carried out by multivariate calibration.

5. The invention of claim 1, wherein said second blend is subjected to radiant energy, has an area of at least about 3 inches in diameter.

6. A process for spectroscopically monitoring binder mix loading of glass fibers, comprising
   (1) providing calibration for spectroscopic instrumentation based on binder mix content of reference samples of known blends of glass fibers and binder mix, by measuring radiant energy penetration of said reference samples in a wavelength spectrum of about 350-2500 nm;
   (2) exposing at least a portion of a blend of fiber glass and binder mix, while said blend is on a static support substrate or a moving support substrate, to radiant energy in a wavelength spectrum of about 350-2500 nm and measuring absorption of such energy as a result of penetration of said blend;
   (3) monitoring measured absorbed radiant energy as a result of penetrating said reference samples, to obtain relative peak intensity of binder mix, as present in each reference sample and processing to convert peak shape to a level of analyte to obtain a value of binder mix content, and
   (4) correlating said value of binder mix content of said blend with said calibrated reference sample to determine differences, if any, between said values and said calibrated reference samples.

7. The invention of claim 6, wherein steps (3) and (4) are conducted on a periodic or continuous basis.

8. The invention of claim 6, wherein said blend of glass fibers and binder mix is provided as a mat.

9. The invention of claim 6, wherein calibration of such spectroscopic instrumentation is carried out by multivariate calibration.

10. The invention of claim 4 or 9, wherein said multivariate calibration utilizes a Partial Least Squares (PLS) algorithm.

11. The invention of claim 4 or 9, wherein said multivariate calibration utilizes a Principle Component Regression (PCR) algorithm.

12. The invention of claim 4 or 9, wherein said multivariate calibration utilizes a Multiple Linear Regression (MLR) algorithm.

13. The invention of claim 1 or 6, wherein said radiant energy wavelength region is 400-2500 nm.

14. The invention of claim 1 or 6, wherein said radiant energy wavelength region is 400-1800 nm.

15. The invention of claim 1 or 6, wherein said radiant energy wavelength region is 400-1000 nm.

16. The invention of claim 1 or 6, wherein said radiant energy wavelength region is 350-1050 nm.

17. The invention of claim 1 or 6, comprising selecting an on-line support substrate conveying system.

18. The invention of claim 1 or 6, comprising selecting a support substrate which is a rotating turntable.

19. The invention of claim 6, wherein said portion of such blend of fiber glass and binder mix subjected to said radiant energy, has an area of at least about 3 inches in diameter.

* * * * *

UNITED STATES PATENT AND TRADEMARK OFFICE
CERTIFICATE OF CORRECTION

PATENT NO.        : 7,641,826 B2                                                Page 1 of 1
APPLICATION NO.   : 11/356175
DATED             : January 5, 2010
INVENTOR(S)       : Reginald A. Mbachu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this

Twenty-first Day of December, 2010

David J. Kappos
*Director of the United States Patent and Trademark Office*